United States Patent
Cao et al.

(10) Patent No.: US 8,131,380 B2
(45) Date of Patent: Mar. 6, 2012

(54) PROBES FOR ELECTRICAL CURRENT THERAPY OF TISSUE, AND METHODS OF USING SAME

(75) Inventors: Michael Cao, St. Petersburg, FL (US); Ronald Newton, Carson City, NV (US)

(73) Assignee: Vascular Technologies, Inc., Tampa, FL (US)

( * ) Notice: Subject to any disclaimer, the term of this patent is extended or adjusted under 35 U.S.C. 154(b) by 1145 days.

(21) Appl. No.: 11/815,617

(22) PCT Filed: Feb. 14, 2006

(86) PCT No.: PCT/US2006/005303
§ 371 (c)(1),
(2), (4) Date: Aug. 6, 2007

(87) PCT Pub. No.: WO2006/088943
PCT Pub. Date: Aug. 24, 2006

(65) Prior Publication Data
US 2008/0208188 A1    Aug. 28, 2008

Related U.S. Application Data

(60) Provisional application No. 60/652,587, filed on Feb. 14, 2005.

(51) Int. Cl.
*A61F 7/00* (2006.01)
*A61F 7/12* (2006.01)
(52) U.S. Cl. ............................ 607/138; 600/245; 606/41
(58) Field of Classification Search .................. 600/245; 606/46; 607/138
See application file for complete search history.

(56) References Cited

U.S. PATENT DOCUMENTS

| | | | | |
|---|---|---|---|---|
| 3,417,746 A | * | 12/1968 | Moore et al. | 600/184 |
| 4,898,169 A | | 2/1990 | Norman et al. | |
| 5,165,387 A | * | 11/1992 | Woodson | 600/184 |
| 5,249,568 A | * | 10/1993 | Brefka et al. | 600/184 |
| 5,688,224 A | * | 11/1997 | Forkey et al. | 600/200 |
| 5,779,686 A | | 7/1998 | Sato | |
| 6,428,473 B1 | * | 8/2002 | Leonard et al. | 600/219 |
| 2003/0130559 A1 | | 7/2003 | Morin | |
| 2006/0009797 A1 | * | 1/2006 | Armstrong | 606/197 |
| 2006/0229595 A1 | | 10/2006 | Newton et al. | |
| 2008/0275301 A1 | * | 11/2008 | Lubowski et al. | 600/130 |

\* cited by examiner

*Primary Examiner* — Roy Gibson
*Assistant Examiner* — Kaitlyn Smith (57) ABSTRACT

Disclosed herein are probes for use in delivering electrical current therapy to a target tissue. In specifically exemplified embodiments, the probes comprise a base comprised of a degradable material so as to prevent the potentially dangerous reuse of the probes. Also disclosed is a surgical tool for use in rectal examination and surgical removal of hemorrhoid tissue. The tool includes an anoscope having a somewhat conical shape wherein the proximal end is larger in diameter than the distal end. The anoscope has a first slot near the proximal end and a second slot near the distal end. An obturator is included that also has a somewhat conical shape. The obturator is smaller in diameter than the anoscope so that it will easily fit within the anoscope. A cylindrical shaped light cover is included as well, which is adapted to engage the first slot of the anoscope. The light cover further includes a receptacle and a lens in its distal end which receives a light.

1 Claim, 11 Drawing Sheets

Fig. 10

PROBES FOR ELECTRICAL CURRENT THERAPY OF TISSUE, AND METHODS OF USING SAME

RELATED APPLICATIONS

This U.S. §371 National Phase patent application bases priority on International Application No. PCT/US2006/005303, filed on Feb. 14, 2006, which in turn bases priority on U.S. Provisional application Ser. No. 60/652,587, filed on Feb. 14, 2005.

BACKGROUND OF THE INVENTION

1. Field of the Invention

The invention relates to novel probes designed for use with an electrical current therapy device to treat hemorrhoids.

2. Description of the Prior Art

Hemorrhoidal disease is one of the most frequent, disabling, and painful conditions of mankind. The consensus of the Advisory Panel of the U.S. Food and Drug Administration defines hemorrhoids as "abnormally large or symptomatic conglomerates of blood vessels, supporting tissues, and overlying mucous membrane or skin of the anorectal area."

It is estimated that one-third of the U.S. population has symptomatic internal hemorrhoids, with an incidence of 50% at age 50 years. Patients frequently postpone examination because of concern of pain associated with a particular treatment modality, hospitalization, cost, and time of disability. Such a delay in evaluation may lead to progression of the hemorrhoidal disease, or late diagnosis of more serious colorectal problems.

Medical procedures for hemorrhoidal treatment have taken many forms. For example, D.C. (direct current) management of hemorrhoidal disease was described in a review published by Wilbur E. Keesey, M. D. in 1934. The topical suppository approach is presently applied to a majority of patients, particularly those with a specific precipitating factor for hemorrhoidal disease (e.g., acute diarrhea episode) and in some instances may be all that is necessary. Necrosis and slough of hemorrhoidal vessels can also, at times, be accomplished by placement of rubber bands over the vessel base with a specific apparatus. This treatment is applicable to those vessels well above the pectinate line to avoid severe pain (a complication in 6 to 10% of patients). Mild to moderately diseased hemorrhoidal vessels are not amenable to this therapy. Injection sclerotherapy is effective for small (grade 1 and 2) bleeding internal hemorrhoids. Submucosal injection of sclerosant produces chemical thrombosis and fixation of the mucosa to the underlying tissue. Sclerotherapy of hemorrhoids is limited to mild to moderate disease and is associated with complications including reaction to the injected material, slough of the overlying mucosa, necrosis, and infection, including submucosal abcess. Cyrosurgery (i.e., application of a metal probe cooled by liquid nitrogen or carbon dioxide) freezes hemorrhoids. Occasionally, local anesthesia is required because of pain. Complications may include imprecise control of the depth of tissue destruction, post-operative pain, and rectal drainage. Surgical excision of hemorrhoidal inflammatory disease has the advantage of removing all associated redundant tissue, including the external component of a particular internal hemorrhoid. However, there are limitations to the amount of excision possible without major adverse sequelae. In a typical patient with many involved vessels, surgery can only approach the most symptomatic-diseased area and is not to be considered curative. The disadvantages of these approaches include pain, expense associated with hospitalization, time of disability, and potential complications, e.g., those associated with anesthesia, surgery proper, and post operative complications, including anal stenosis.

The treatment and correction of hemorrhoids may deploy one or more electrodes for providing radio frequency (RF) energy, microwave energy, or thermal energy to shrink a dilated vein in order to change the fluid flow dynamics and to restore the competency of the venous valve and the proper function of the vein. See U.S. Pat. No. 4,898,169 ('169 Patent).

Incompetent valves in the venous system can occur with vein dilation. Separation of the cusps of the venous valve at the commissure may occur as a result thereby leading to incompetence. Another cause of valvular incompetence occurs when the leaflets are loose and elongated. Loose leaflets of the venous valve results in redundancy, which allows the leaflets to fold on themselves and leave the valve open. These loose leaflets may prolapse, resulting in reflux of blood in the vein. When the venous valve fails, there is an increased strain and pressure on the lower venous sections and overlying tissues sometimes leading to additional valvular failure.

Advancements in the art have been made to treat and cure hemorrhoidal lesions. The method disclosed in the '169 Patent is particularly effective, painless and safe, when used properly. The probes disclosed in the '169 Patent are intended for single use only, and are clearly marked as such. However, the inventors have noted that some physicians attempt to sterilize and reuse the probes. Reuse of the probes in this way is not advisable, since it may increase the risk of generating nosocomial infections in the patient. Proper disposal of used probes are vital to ensuring the safety of patients.

SUMMARY OF THE INVENTION

According to one aspect, the invention pertains to a probe for use with an instrument designed for direct current electrical therapy of hemorrhoidal lesions or the like in a patient. See for example, U.S. Pat. No. 4,898,169. According to a specific aspect, the probe is adapted for use with an instrument for direct current electrical therapy of hemorrhoidal lesions or the like in a patient, employing a D.C. electric generator, a grounding pad for the patient, and an instrument hand piece for support of the probe and control of the level of direct current, and the probe comprises a base having a proximal end and a distal end, wherein said base is comprised of a degradable material. The degradable material is subject to degradation upon sterilization such as by autoclaving. Extending from the distal end of the base is at least one elongated monopolar probe electrode comprising a proximal end and distal end, wherein the distal end terminates in a distal tip adapted for electricity-conducting engagement with a hemorrhoidal lesion. At the proximal end of the probe base is a coupler attached to or integrated with the base which is designed for engaging the probe base to the handpiece in electricity-conducting engagement.

In another embodiment, the subject invention pertains to a monopolar probe adapted for use with an instrument for directing current electrical therapy. The probe comprises a length of continuous electricity conducting material comprising a first end and a second end and an elongated body between said first and second ends. At a location along said elongated body, the elongated body comprises a bent region. The elongated body between said first end and said bent region forms a first projecting member, and a second projecting member between said second member and a bent region. A base is secured to the first and second projecting members. The bent region and first and second projecting members are configured such that the first and second ends are into tissue engaging proximateness with each other. The term "tissue engaging proximateness" broadly refers to the ability of the first and second ends to contact a target tissue such that the first and second ends achieve an electricity conducting engagement with such target tissue. In one embodiment, tissue engaging proximateness corresponds to the first and second ends being a distance from each other of any length between 0.2 to 150 mm from each other. In a specific embodiment, the first and second ends is a distance from each other of any length between 1 to 30 mm. In a preferred embodiment, the distance of the first and second ends from each other is a distance of 3 mm to 15mm.

As noted above the base of probe embodiments of the subject invention may be comprised of a degradable material that is degradable upon being subjected to autoclaving, the common sterilizing procedure in most medical offices, or other form of heated water treatment. Those skilled in the art will appreciate that such degradable material may include conventional degradable plastics, such as but not limited to, PVA, polyhydroxyalkanoate, poly-lactide, or polyethylene, may be adapted for use as the material for the base so long as it is tailored to degrade upon treatment with heated water. In a specific embodiment, the biodegradable plastic is PVOH based polymer. See Proceedings of the 8th Annual Global Plastics Environmental Conference, "Plastics Impact on the Environment", Society of Plastics Engineers, Detroit MI, p. 360, 14 Feb. 2002, RECENT ADVANCES IN THERMOPLASTICALLY-PROCES SABLE POLYVINYL ALCOHOL-BASED MATERIALS. One specific brand of such plastic is the Depart C-10 Series of plastics (Adept Polymers Limited, Unit 7, and Woodrow Way, Fairhills Industrial Estate, Irlam, Manchester, M44 6ZQ).

BRIEF DESCRIPTION OF THE DRAWINGS

Further advantages and features of the present invention can be gathered from the following description of the preferred embodiment relative to the attached drawings, wherein:

FIG. 3 is a plan view of an instrument probe comprising a degradable base, while

FIG. 4 is a diagram depicting the stages of construction of a probe embodiment according to one embodiment of the subject invention.

FIG. 5 is a diagram depicting stages of construction of another probe embodiment; FIG. 5A top view showing the implementation of projecting members and attachment to a bridge and lug; FIG. 5B is a top view showing the attached projecting members, bridge and lug with portions of projecting members comprising an insulating layer; and FIG. 5C is a top view of the assembly shown in FIG. 5B with a base formed around the bridge and portions of the lug and projecting members.

DETAILED DESCRIPTION OF THE PREFERRED EMBODIMENT

Figure 1:
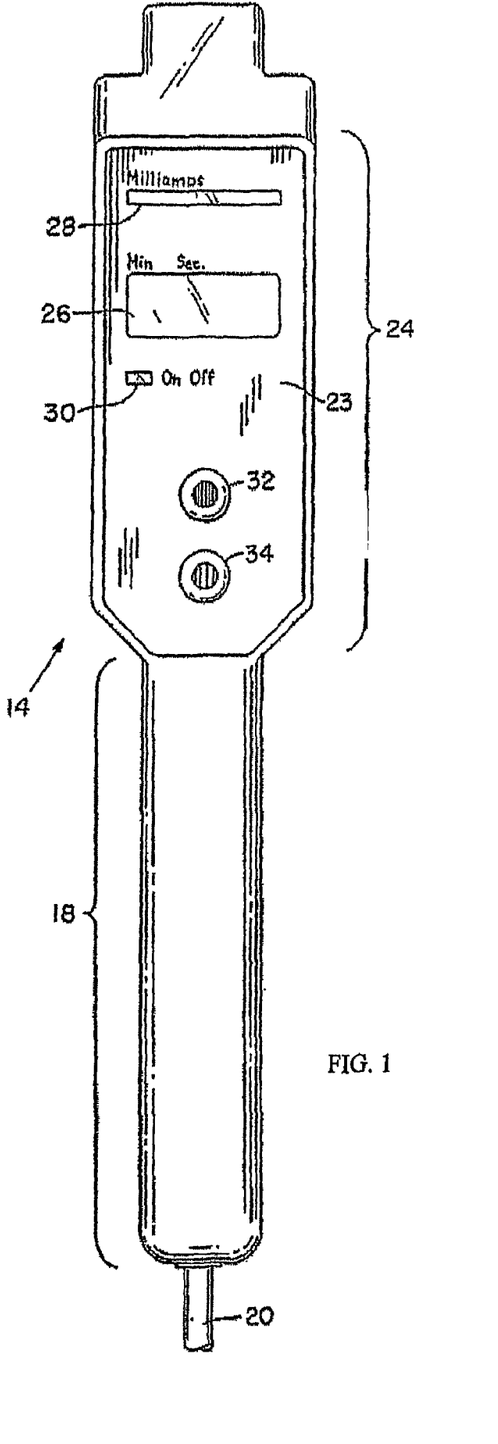
FIG. 1 is a plan view of a handpiece for implementation of embodiments of the subject invention.
Figures 2, 2A:
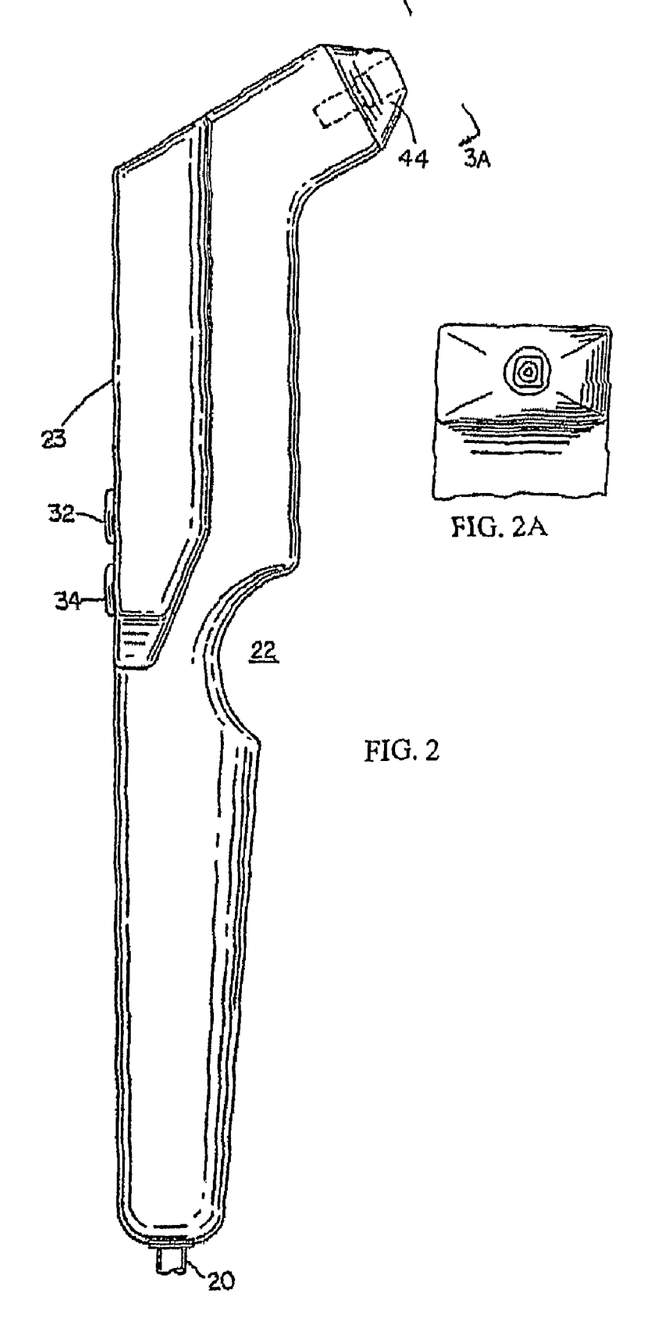
FIG. 2 is a side view of the handpiece of FIG. 1.
FIG. 2A is a plan view of the probe receptacle of the handpiece of FIG. 2, taken at 3A-3A of FIG. 2.

FIG. 1 shows one embodiment of an electrical current delivery system in which the probe embodiment of the subject invention may be employed. See U.S. Pat. No. 4,898,169 (which is incorporated by reference in its entirety). The system comprises a handpiece 14 having a lower handle portion 18 from which extends a connector cord 20 to the base unit 12, and, as shown in FIG. 2, includes a rear indentation 22 for receiving the fore finger of the user in gripping engagement. The planar face surface 23 of the handpiece, on the upper patient treatment portion 24, contains display elements of, e.g., elapsed time of treatment (LED numeric display 26), level of treatment current (LED bar graph 28), and circuit status indicator (on/off display 30). The upper patient treatment portion further contains switches 32, 34 for respectively incrementally increasing and decreasing the level of D.C. current through the probe and, when activated by the surgeon simultaneously, e.g., by pressing with his thumb, as described below, for ceasing flow of electricity. The handpiece face surface 23 is sealed against entry of fluid into the handpiece during cleaning between procedures. The distal end 44 comprises an aperture 40 defined therein to receive the probe.

Figure 3:
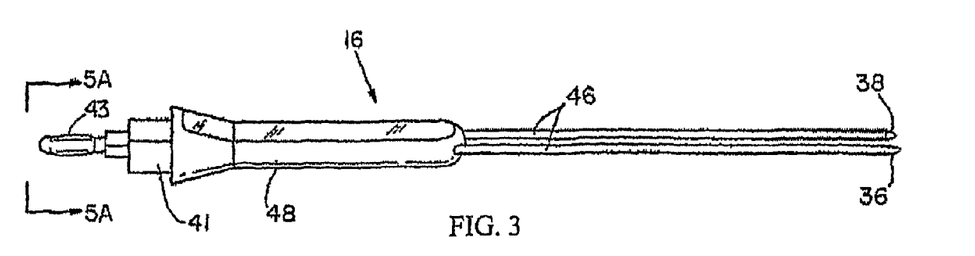
Figure 3A:
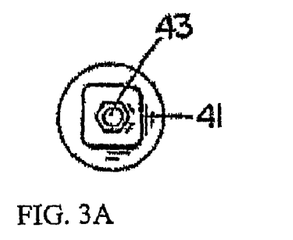
FIG. 3A is an end view of the probe base segment taken at 5A-5A of FIG. 3.

Referring to FIGS. 3 and 3A, the probe 16 consists of a pair of elongated, electrically-conductive electrodes 36, 38 extending to sharpened distal tips from a probe base 48. Extending in a proximal direction from the probe base is a keying block 41, e.g., of square cross-section with radiused corners (FIG. 3A), sized to fit snugly within the aperture 40 (FIG. 2) provided in the distal end 44 of handpiece 14. A plug 43 adjacent to the keying block 41 firmly mounts the probe 16 to the handpiece 14. The probe electrodes are clad in nonconductive sleeves 46 over their distal portions to prevent inadvertent tissue contact, but to minimize obstruction to the surgeon's view of the treatment site. The proximal portions of the electrodes are encased in probe base 48, e.g., of injection molded plastic. The keying block 41 is constructed to be received into the aperture 40 at four orientations (90° rotations), selected by the surgeon depending upon the rectal quadrant to be treated. FIG. 2A shows a frontal view along the plane 3A-3A indicated in FIG. 2 and shows the aperture 40 into which the keying block is inserted.

Figures 4A, 4B:
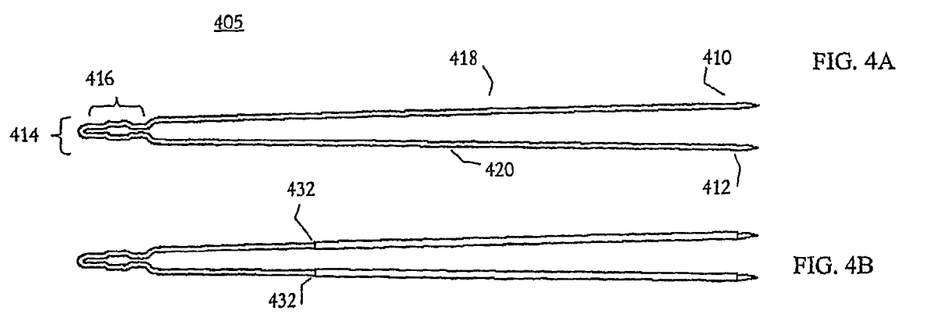
FIG. 4A showing a length of conductive material.
FIG. 4B showing the length with insulating layer thereon.

FIGS. 4A-D show the different phases of production of a new probe design embodiment 400. FIG. 4A shows a length of electricity conducting material 405 comprising a first end 410 and second end 412. The ends are preferably beveled to form a point. Between said first end 410 and second end 412 is an elongated body of material that comprises a bent region 414. Upstream from the bent region 414, i.e., toward the respective first and second ends 410, 412 from the bent region 414 is a jack region 416 configured to fit into a female end of a conventional banana jack. The bent region 414 and jack region 416 are designed such that there are a first and second elongated projecting members 418, 420 spanning from the jack region 414 to the first and second ends 410, 412, respectively. The first and second projecting members 418, 420 are shown to be straight but may contain curves or other angles so long as the first and second ends 410, 412 may be brought in tissue engaging proximateness with each other upon the base 430 being associated with said first and second projecting members 418, 420.

The length of electricity conducting material may be a metal wire, such as stainless steel, copper, etc. The metal wire is heat annealed at approximately the center point of the wire. This wire is then bent about 180 degrees to provide an offset of the ends (i.e., one point slightly lower than other). The bending is achieved through use of a bending fixture (not shown).

Shrink tubing 432 (e.g., 3M FP-301) is placed over each projecting member 418, 420 to their respective ends where the bevel of the point starts (see FIG. 4B). The length 405 with shrink tubing 432 thereon is placed into an oven at a temperature and time sufficient to shrink the tubing around the wire. Typically, 15 minutes @ 300-500 degrees F is sufficient for this purpose.

Figures 4C, 4D:
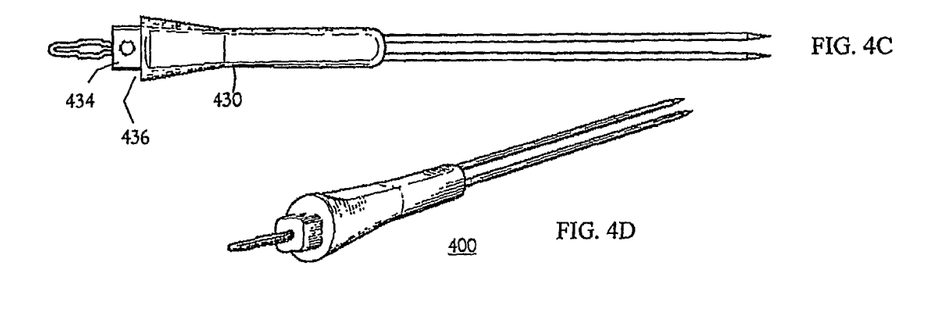
FIG. 4C showing the length of FIG. 4B with based formed thereon.
FIG. 4D showing a perspective view of the embodiment shown in FIG. 4C.

After shrinking the tubing 432, the base 430 is associated with the first and second projecting members 418, 420. In one embodiment this is achieved through plastic mold injecting. The molds are designed to seal around the projecting member 418, 420 and a portion of the shrink tubing 432. In a particularly preferred embodiment, the degradable plastic used for the base 430 is C10 made by Adept Polymers, Ltd, and the injection is conducted @ 11,000 PSI, @ 350-400 degrees F. The plastic injection forms a 4 sided keying block 434 with a physical stop 436. This is intended for mating with the handpiece described above. The 4-sided insert allows for the positioning of the probes in two positions vertical and two positions horizontal.

The final packaging of the probe comprises a plastic guard to prevent accidental puncture and a gas permeable sleeve for sterilization. Due to the plastic being water-soluble, gas sterilization or E bean is used. Steam sterilization is prohibited.

Figures 5, 5A, 5B, 5C:
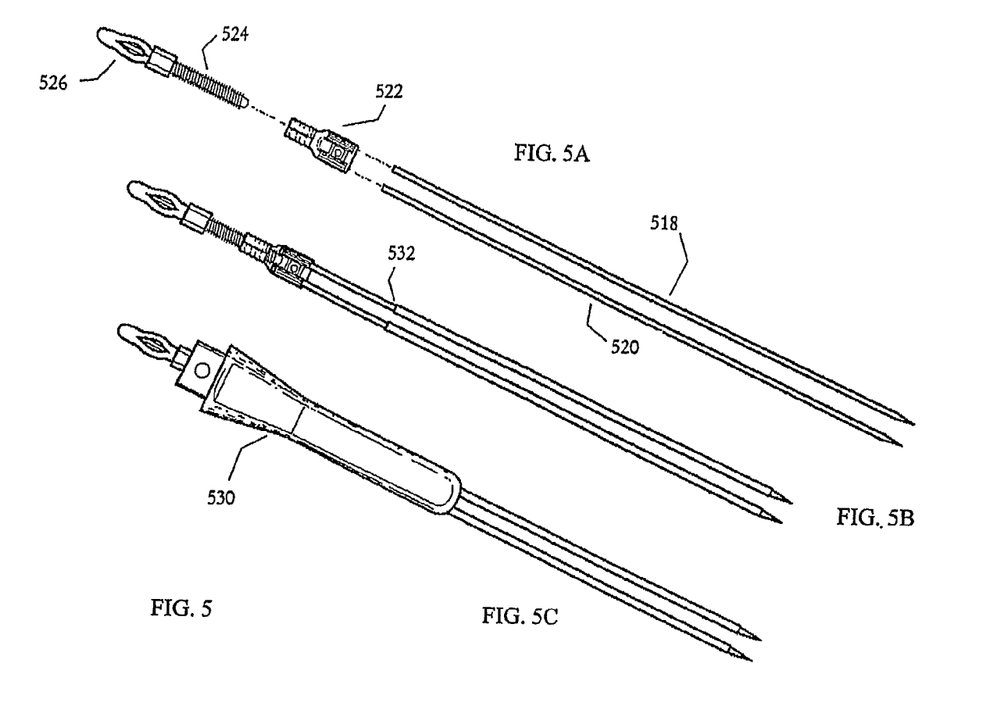

FIGS. 5A-C shows the construction of a probe 500 according to an alternate embodiment of the subject invention. The probe 500 comprises a first and second projecting members 518, 520 which are attached to a bridge 522. A lug 524 comprising a banana jack 526 is attached to the bridge and an insulating layer 532, e.g., heat shrink tubing, is applied to the first and second projecting members, 518, 520. A base 530 is formed around the bridge 522 and portions of the lug 524 and projecting members 518, 520. The base 530 is formed of a degradable material.

In another embodiment, the invention pertains to a method of making a probe useful for delivering electrical current to a target tissue. The method comprises obtaining a length of electricity conducting material. The length of material comprises a first end and a second end and an elongated body spanning between said first and second ends. The length is bent at a location along the elongated body to produce a first and second projecting members between the bent region and the first and second ends, respectively. A base is put upon said first and second projecting members such that it is secured to and supports the members with the support member extending from the distal end of the base. The base preferably comprises a keying portion extending from its proximal end for engagement to a receiver defined in a electrical current delivery device. Extending from the proximal end of the keying portion is a portion of the first and second projecting members configured for electricity conducting engagement with a female jack on said electrical current delivery device.

A feature of another embodiment provides an improved light weight surgical tool that is disposable after use and one that is easy to use for hemorrhoid treatment. Another feature is to provide an improved surgical tool that is less discomforting to the patient than other such tools currently available on the market today. Yet another feature of an embodiment is to provide an improved surgical tool that offers unhampered room for manipulation of instruments while performing an operation therein. Still another feature of an embodiment is to provide an improved surgical tool that uses a readily available, adjustable battery-powered light source which is rechargeable.

According to one embodiment, a surgical tool is provided for use in rectal inspection and surgical removal of hemorrhoid tissue. The surgical tool includes an anoscope having a somewhat tapered shape with a proximal end larger in diameter than the distal end. The anoscope has a first slot near the proximal end for receiving a light cover and a second slot near the distal end for isolation and exposure of hemorrhoid tissue. An obturator, which is smaller in diameter than the anoscope so that it will easily fit within the anoscope, is included. A light cover is included as well, which has an open end and a second closed end. The light cover includes a flange extending around the periphery near the closed end, wherein the flange is disposed at an angle with the longitudinal axis of the light cover and includes a groove around the periphery thereof for engaging the first slot of the anoscope. The closed end further includes a lens in one end. The lens is configured for passage of light by a light source disposed within the light cover, whereby light is disbursed within the surgical tool for enabling inspection and surgical operations therein.

Other features and advantages of the present invention will become readily apparent to those skilled in the art from the following detailed description, wherein is shown and described only the preferred embodiment of the invention, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive, and what is intended to be protected by Letters Patent is set forth in the appended claims. The present invention will become apparent when taken in conjunction with the following description and attached drawings, wherein like characters indicate like parts, and which drawings form a part of this application.

Figure 6:
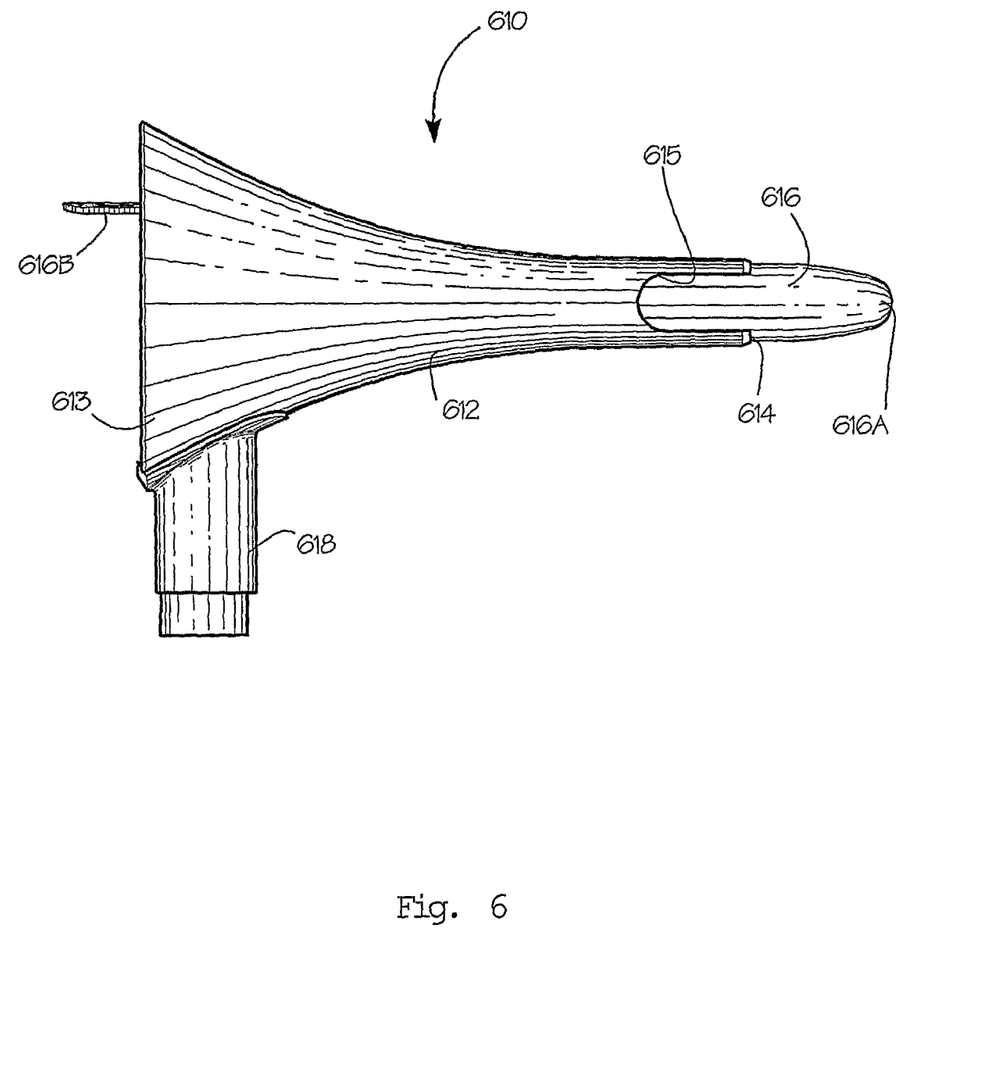
FIG. 6 is an elevational view of the surgical tool assembly in accordance with the present invention.

Referring to FIG. 6, a perspective view of the surgical tool assembly 610 of the present invention is shown. The tool assembly 610 comprises three basic parts which are preferably made of an inexpensive material suitable for disposal after use, such as but not limited to a plastic. First, there is an anoscope member 612 (FIG. 7) typically having a somewhat conical shape. A slot 615 is formed near the distal end of the anoscope member 612, which will be used for isolation of hemorrhoid tissue once the obturator 616 is removed as will be explained further hereinafter. The slot 615 is designed to allow an internal hemorrhoid to extend through the slot so that it can be manipulated for treatment. A second slot 611 is formed in the proximal end 613 for receipt of a light cover 618.

Figure 7:
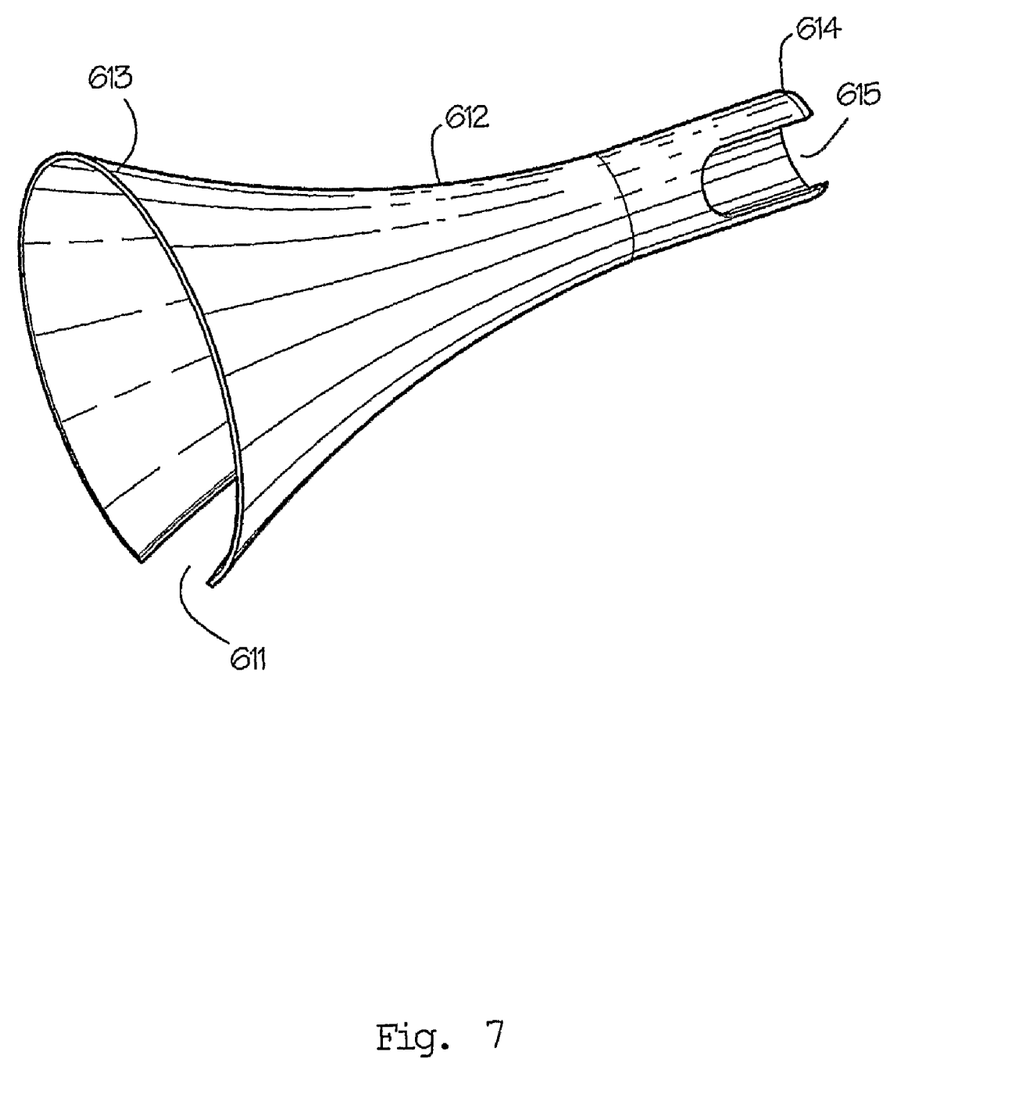
FIG. 7 is a perspective view of the anoscope member itself showing a slot for a light source at the proximal end thereof and another slot at the distal end for isolation and exposure of hemorrhoid tissue.

In accordance with a specific embodiment, the member 612 is approximately 4.75 inches long, with a proximal end 613 having a diameter of 2 inches and a distal end 614 having a diameter of 0.89 inches. The taper is on an approximately 8 inch radius. The slot 615 according to this specific embodiment is approximately 0.5 inches wide and 1.25 inches long. In accordance with a preferred embodiment the slot 611 is displaced 90 degrees from the slot 615 in order to allow for probes to be away from the light source during a surgical operation thereby giving the physician more flexibility. The foregoing dimensions and values are provided merely to disclose the best mode. Those skilled in the art will appreciate that different structures and parts of the assembly can be designed according to numerous variations in size and dimensions.

Figure 8:
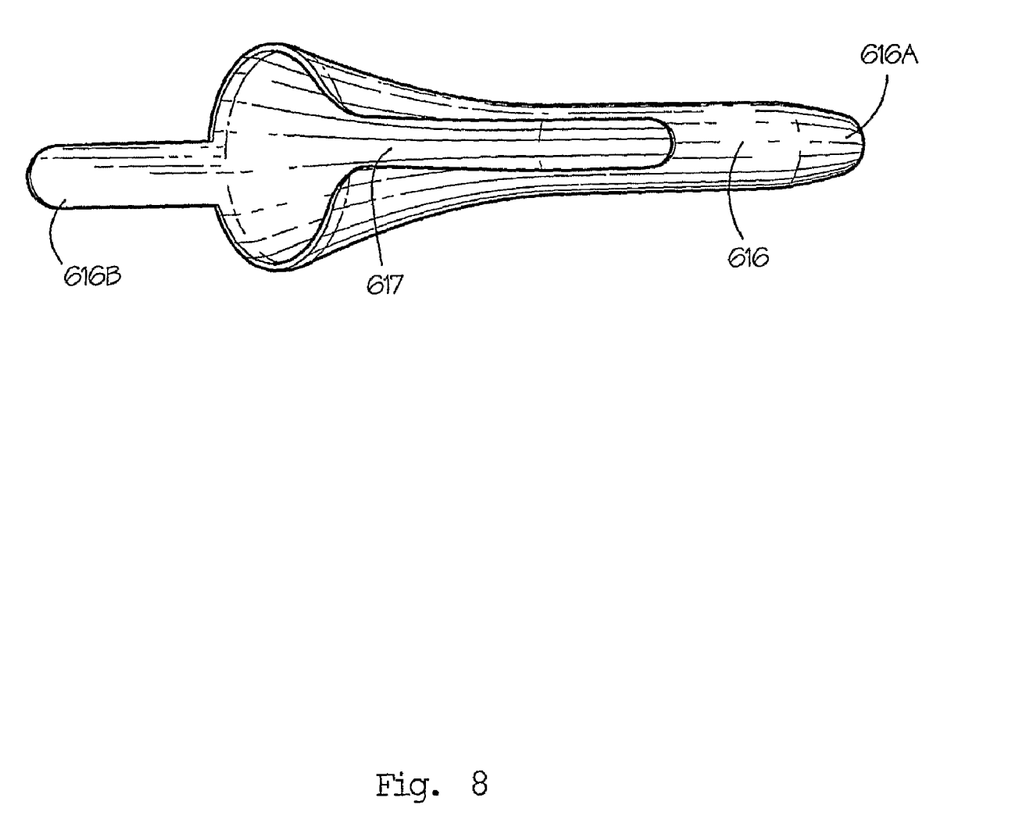
FIG. 8 is a perspective view of the obtuator member of the present invention, which nests within the anoscope member as shown in the surgical tool assembly of FIG. 6.

The second basic part is an obturator member 616 (FIG. 8), which slides within the anoscope member 612 and nests into place as shown in FIG. 6. The obturator 616 purposely has a loose fit within the anoscope member 612 in order to allow for gas to pass and not to create suction when removed. It has a bullet end 616A on the distal end thereof, which eases insertion of the assembly 610 into the rectum of the patient. A tab 616B extends from the proximal end of the obturator member 616, which allows for easy removal from the anoscope member 612.

The third basic part of the surgical tool 610 is a light cover 618 (FIG. 9), which is designed to protect a lamplight source from fecal or fluid contamination. The light cover 618 becomes a permanent part of the surgical tool assembly 610 when assembled. It snaps into the proximal end slot 611 of the anoscope member 612, and it is disposed of along with the other two parts described above, i.e., the anoscope member 612 and the obturator 616.

Referring again to FIG. 8, a perspective view of the obturator 616 is shown. A slot 617 is formed along one side of the obturator (beginning at the proximal end 616C) in order to allow for clearance of the light cover 618. During use, the light (not shown) is turned on with the obturator 616 in place. The surgical tool 610 is inserted into the rectum of the patient and the obturator 616 is next removed by use of the tab 616B. This now allows for examination within the anoscope member 612. If another quadrant needs to be examined, the obturator 616 is reinserted and the surgical tool 610 is turned as required. The above-described process is repeated as necessary.

Figure 9:
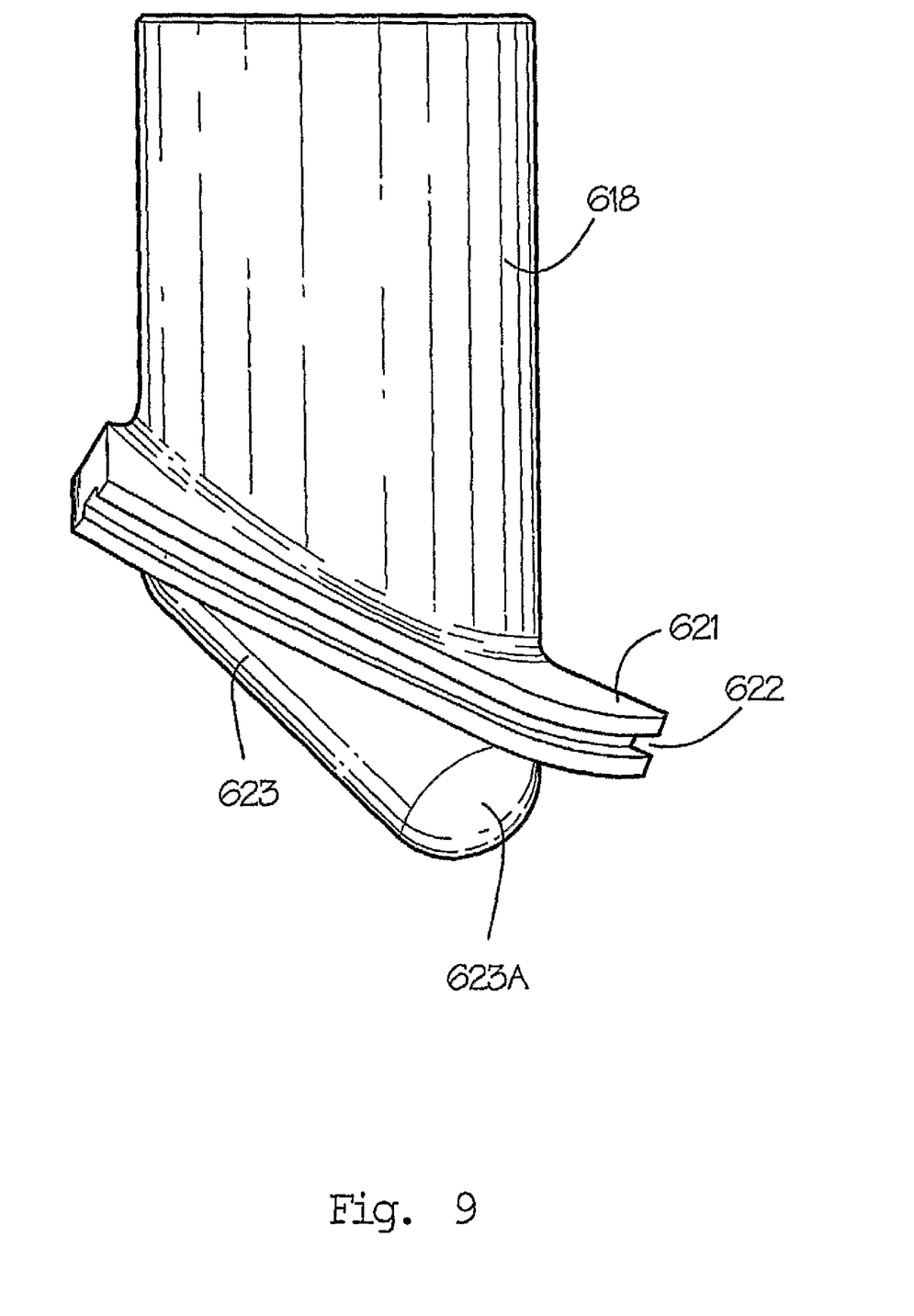
FIG. 9 is an elevational view of the light cover for the present invention, which is inserted into the slot of the anoscope at the proximal end thereof.
Figure 9A:
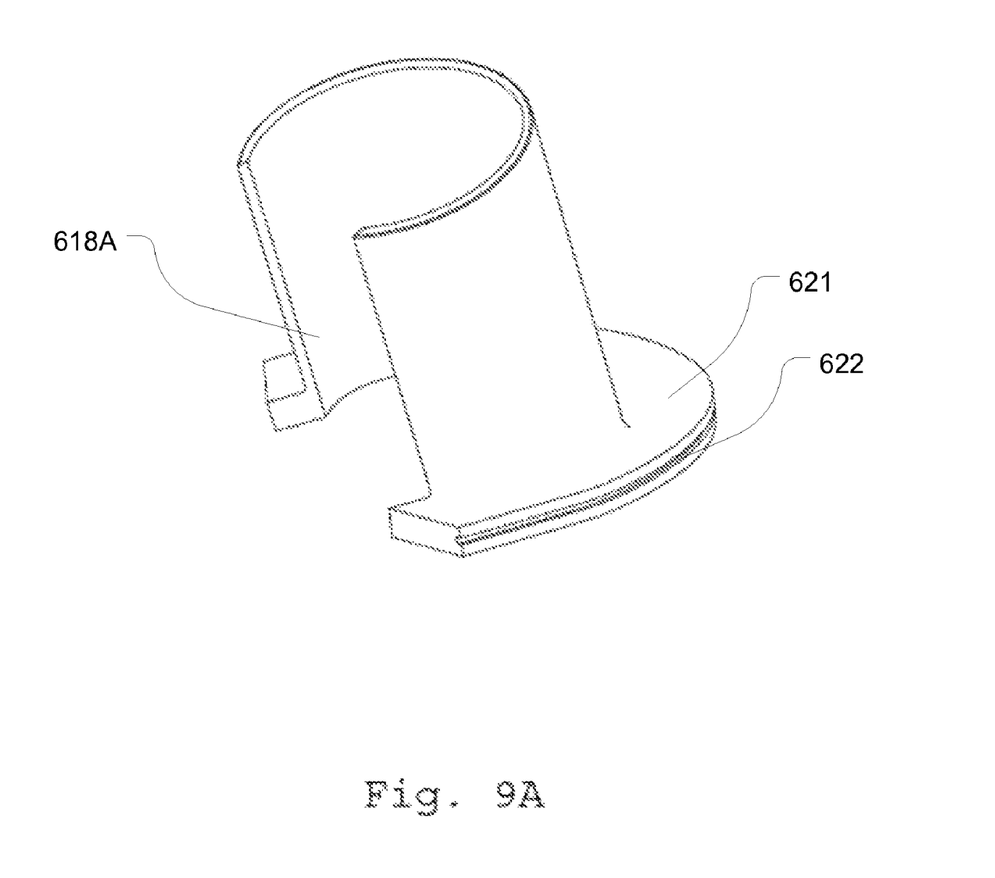
FIG. 9A is perspective view of the light cover.

Referring now to FIG. 9, a perspective view of the light cover 618 is shown. The light cover 618 includes an open proximal end 618A, and near the distal end thereof a flange extension 621 is disposed at an angle with the longitudinal axis of the cover 618. The flange 621 includes a groove 622 around the periphery thereof for slidably engaging the anoscope member 612 in the slot 620. The distal end of the cover 618 is closed and a receptacle 623 is formed thereon for receipt of the light source. The angle of the flange 621 combined with the angle of the receptacle 623 compensate for the sloped side of the anoscope 612 such that light is directed toward the distal end 614 of the anascope 612.

As alluded to hereinabove, the anoscope member 612, the obturator 616 and the light cover 618 are all preferably made of a plastic material. The light cover has a receptacle 623 for receiving a light bulb. Further, The light cover 618 has at least a transparent portion 623A, such as a lens, to allow a beam of light to shine inside the distal end of the anoscope member 612. In a specific embodiment, the transparent portion 623A is a lens integrated or attached at the distal end of the receptacle 623, which enables disbursement of light within the surgical tool once a light source is inserted into the cover 618.

Figure 10:
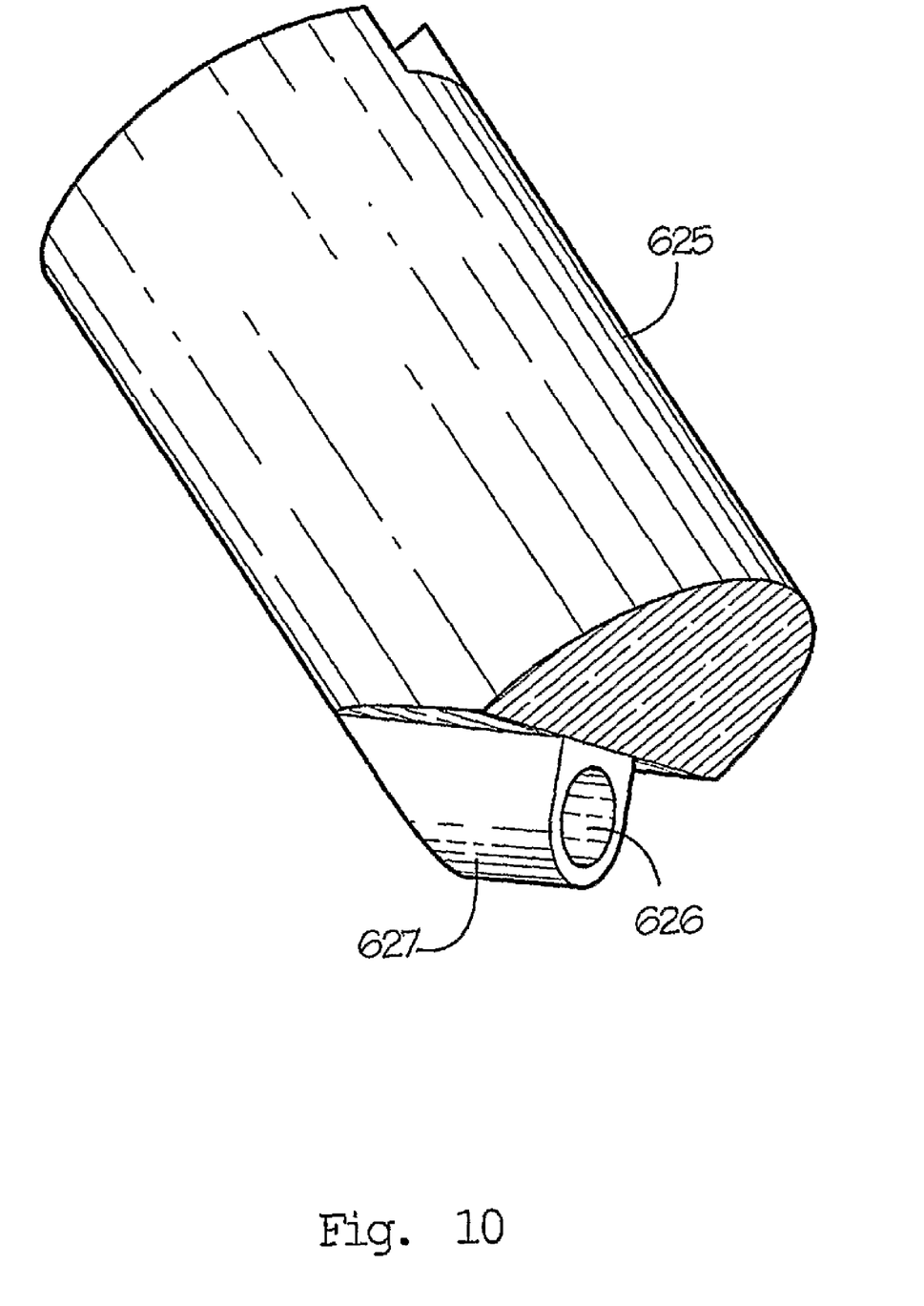
FIG. 10 is a perspective view of an adapter for a light source.

Referring now to FIG. 10, a perspective view of an adapter 625 for a light source, such as a Welsh Allyn rechargeable handle (not shown) that is used in many physicians offices either as an otoscope or a laryoscope, or other appropriate light sources. A pocket 627 with an open distal end 626 is formed in the distal end of the adapter 625 for receipt of a light bulb (not shown). Typically, electrical conductors to the light bulb from contact pads are embedded within the adapter. The contact pads are disposed for ohmic contact with corresponding contact pads on the rechargeable handle, all in a conventional manner. The adapter 625 is not intended to be disposable, and is saved for repeated use. In an alternative embodiment, a camera is also disposed within the adapter 625 such that its lens is disposed at the open distal end 626. Typically, the camera lens and light bulb share space in the pocket 627. The camera may be integrated into the light source similar to a camera currently available mobile phones. Alternatively, the camera may be connected to a recorder and/or screen for taping or digital recording and/or real time viewing. This feature may be important for educational purposes or record-keeping.

Finally, while various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference to the extent they are not inconsistent with the teachings herein.

What is claimed is:

1. A surgical tool for use in rectal inspection and surgical removal of hemorrhoidal tissue therefrom, said surgical tool comprising:
    a) an anoscope having a substantially conical shape with a proximal end and a distal end wherein said proximal end is larger in diameter than said distal end, and further having a first slot near said proximal end and a second slot near said distal end, said second slot being located 90 degrees from said first slot;
    b) an obturator also having a substantially conical shape with a proximal end and a distal end, said obturator being of a size smaller in diameter than said anoscope so that said obturator fits within said anoscope, said obturator including a slot formed in one side thereof beginning at the proximal end;
    c) a cylindrical shaped light cover with a longitudinal axis and having an open proximal end and a closed distal end, said light cover including a flange extending around the periphery near said closed end, said flange being disposed at an angle with said longitudinal axis and including a groove around the periphery thereof for engaging said first slot of said anoscope, said closed end further comprising a receptacle that comprises a lens in one end thereof, said receptacle being disposed for receipt of a light source, whereby light is disbursed within said surgical tool for enabling inspection and surgical operations therein when a light source is inserted into said light cover, and
    d) a monopolar probe passing through the obturator and exposed at a distal end of the obturator slot and at the second slot of the anoscope so that tissue captured in the second slot can be excised wherein the probe comprises:
        a base having a proximal end and a distal end, wherein the base is comprised of a water-degradeable material;
        extending from the distal end of the base, at least one elongated monopolar probe electrode comprising a proximal end and distal end, wherein the distal end terminates in a distal tip adapted for electricity-conducting engagement with a hemorrhoidal lesion; and
        a keying block extending from the proximal end of the base configured for engaging the probe base to a handpiece in electricity conducting engagement.

* * * * *